United States Patent [19]
Lum et al.

[11] Patent Number: 5,779,643
[45] Date of Patent: *Jul. 14, 1998

[54] IMAGING GUIDEWIRE WITH BACK AND FORTH SWEEPING ULTRASONIC SOURCE

[75] Inventors: Paul Lum, Los Altos; Edward Verdonk, San Jose, both of Calif.

[73] Assignee: Hewlett-Packard Company, Palo Alto, Calif.

[*] Notice: The term of this patent shall not extend beyond the expiration date of Pat. No. 5,647,367.

[21] Appl. No.: 757,040

[22] Filed: Nov. 26, 1996

[51] Int. Cl.$^6$ .................................................. A61B 8/12
[52] U.S. Cl. ........................... 600/462; 600/585; 29/25.35
[58] Field of Search ........................ 128/662.06, 662.03; 600/462.1, 585; 29/25.35

[56] References Cited

U.S. PATENT DOCUMENTS

| | | |
|---|---|---|
| 4,794,931 | 1/1989 | Yock . |
| 4,899,757 | 2/1990 | Pope, Jr. et al. . |
| 5,000,185 | 3/1991 | Yock . |
| 5,176,141 | 1/1993 | Bom et al. . |
| 5,240,003 | 8/1993 | Lancee et al. . |
| 5,271,402 | 12/1993 | Yeung et al. . |
| 5,368,035 | 11/1994 | Hamm et al. ............... 128/662.06 |
| 5,377,685 | 1/1995 | Kazi et al. .................. 128/662.06 |
| 5,497,782 | 3/1996 | Fugoso ........................ 128/772 |
| 5,505,088 | 4/1996 | Chandraratna et al. ....... 128/662.06 |
| 5,507,294 | 4/1996 | Lum et al. . |
| 5,509,418 | 4/1996 | Lum et al. . |
| 5,517,989 | 5/1996 | Frisbie et al. ................ 128/642 |
| 5,520,189 | 5/1996 | Malinowski et al. ........ 128/662.03 |
| 5,546,984 | 8/1996 | Hamm et al. ............... 128/662.06 |

OTHER PUBLICATIONS

Sopori, A New Defect Etch for Polycrystalline Silicon, J. Electrochem. Soc.: Solid–State Science and Technology, vol. 131, No. 3, Mar. 1984, pp. 667–672.

Bergeron, et al., Controlled Anisotropic Etching of Polysilicon, Solid State Technology, Aug. 1982, pp. 98–103.

Mandurah, et al., A Model for Conduction Inpolycrystalline Silicon—Part 1: Theory, IEEE Transactions on Electron Devices, vol. ED–28, No. 10, Oct. 1981, pp. 1163–1170.

Bean, Anisotropic Etching of Silicon, IEEE Transactions on Electron Devices, vol. ED–25, No. 10, Oct. 1978, pp. 1185–1193.

Robbins, et al., Chemical Etching of Silicon, Journal of the Electrochemical Society, vol. 107, No. 2, Feb. 1960, pp. 108–111.

Declercq, A New C–MOS Technology Using Anisotropic Etching of Silicon, IEEE Journal of Solid–State Circuits, vol. SC–10, No. 4, Aug. 1975, pp. 191–196.

Tenney, et al., Etch Rates of Doped Oxides in Solutions of Buffered HF, J. Electrochem. Soc.: Solid–State Science and Technology, vol. 120, No. 8, Aug. 1973, pp. 1091–1095.

Kamins, et al., Diffusion of Impurities in Polycrystalline Silicon, J. Appl. Phys., vol. 43, No. 1, Jan. 1972, pp. 83–91.

(List continued on next page.)

*Primary Examiner*—Francis Jaworski
*Attorney, Agent, or Firm*—Philip S. Yip

[57] ABSTRACT

An imaging guidewire for imaging tissues from inside a patient's body cavity. The imaging guidewire includes an elongated main body portion and an end portion. The end portion has a housing near to the guidewire's distal end, an ultrasonic beam emitting assembly having a pivotable part, and a driver for producing a pivotal motion on the pivotable part. The housing has a portion that is acoustically transparent. The pivotable part is movable and is operatively connected to the housing. The pivotable part can either have on it a transducer for emitting ultrasound or a reflector for reflecting ultrasound. In either case, when the pivotable part pivots it sweeps ultrasonic energy over a selected angle. The driver is located near to the transducer such that all driving motions for driving the pivotal motion occur near the distal end of the imaging guidewire.

23 Claims, 10 Drawing Sheets

OTHER PUBLICATIONS van Gelder, et al., The Etching of Silicon Nitride in Phosphoric Acid with Silicon Dioxide as a Mask, J. Electrochem. Soc.: Solid–State Science, vol. 114, No. 8, Aug. 1967, pp. 869–872.

Judy, et al., Batch–Fabricated, Addressable, Magnetically Actuated Microstructures, Solid–State Sensor and Actuator Workshop, Hilton Head, SC, Jun. 2–6, 1996, pp. 187–190.

Judy, et al., Magnetic Microactuation of Polysilicon Flexure Structures, Journal of Microelectromechanical Systems, vol. 4, No. 4, Dec. 1995, pp. 162–169.

Judy, et al., Fabrication Processes for Magnetic Microactuators with Polysilicon Flexures, The 4th International Symposium on Magnetic Materials, Processes, and Devices, Chicago, IL, Oct. 8–13, 1995, 2–page paper.

Judy, et al., Magnetic Microactuation of Torsional Polysilicon Structures, The 8th International Conference on Solid–State Sensors and Actuators, Stockholm, Sweden, Jun. 25–29, 1995, pp. 332–335.

Liu, et al., A Micromachined Permalloy Magnetic Actuator Array for Micro Robotics Assembly Systems, The 8th International Conference on Solid–State Sensors and Actuators, and Eurosensors IX, Stockholm, Sweden, Jun. 25–29, 1995, pp. 328–331.

Liu, et al., Out–of–Plane Permalloy Magnetic Actuators for Delta–Wing Control, Proc. IEEE Micro Electro Mechanical Systems, Amsterdam, The Netherlands, Jan. 29–Feb. 3, 1995, pp. 7–12.

Garabedian, et al., Microfabricated Surface Plasmon Sensing System, Sensors and Actuators A, 43 (1994), pp. 202–207.

Guckel, et al., A First Functional Current Excited Planar Rotational Magnetic Micromotor, Proc. IEEE Micro Electro Mechanical Systems, Fort Lauderdale, FL, Feb. 7–10, 1993, pp. 7–11.

Ahn, et al., A Planar Variable Reluctance Magnetic Micromotor with Fully Integrated Stator and Wrapped Coils, Proc. IEEE Micro Electro Mechanical Systems, For Lauderdale, FL, Feb. 7–10, 1993, pp. 1–16.

Richards, et al., Surface–Plasmon Excitation Using a Polarization–Preserving Optical Fiber and an Index–Matching Fluid Optical Cell, Applied Optics, vol. 32, No. 16, Jun. 1, 1993, pp. 2901–2906.

Wagner, et al., Microactuators with Moving Magnets for Linear, Torsional or Multiaxial Motion, Sensors and Actuators A, 32 (1992), pp. 598–603.

Pister, et al., Microfabricated Hinges, Sensors and Actuators A, 33 (1992), pp. 249–256.

Ahn, et al., A Fully Integrated Micromagnetic Actuator with a Multilevel Meander Magnetic Core, 1992 IEEE, 0–7803–0456–X/92, pp. 14–18.

Wagner, et al., Microfabricated Actuator with Moving Permanent Magnet, 1991 IEEE, CH2957–9/91/0000–0027, pp. 27–32.

Tang, et al., Electrostatic–Comb Drive of Lateral Polysilicon Resonators, Sensors and Actuators, A21–A23 (1990), pp. 328–331.

Steinbruchel, et al., Mechanism of Dry Etching of Silicon Dioxide, J. Electrochem. Soc.: Solid–State Science and Technology, vol. 132, No. 1, Jan. 1985, pp. 180–186.

Tabata, O., "PH–Controlled TMAH Etchants For Silicon Micromachining", 1996, Sensors and Actuators A, 53, pp. 335–339.

Wagner, et al., Microactuators with Moving Magnets for Linear, Torsional or Multiaxial Motion, Sensors and Actuators A, 32 (1992), pp. 598–603.

IMAGING GUIDEWIRE WITH BACK AND FORTH SWEEPING ULTRASONIC SOURCE

FIELD OF THE INVENTION

The present invention relates to imaging guidewires, more particularly, to intravascular imaging guidewires that scan tissues surrounding the imaging guidewire by mechanically moving a transducer in the guidewire.

BACKGROUND

For many diseases, physicians have to access restricted areas in a patient's body. For example, a catheter may need to be inserted into a blood vessel for angioplasty or atherectomy. A guidewire, over which the catheter can be slid, provides a means for introducing the catheter to the desired location. Because the body passageway, e.g., an artery, into which a guidewire is inserted, can often be tortuous, the ability to image the surroundings as the guidewire is being inserted is beneficial for reducing trauma to the patient. Ultrasonic imaging has been used in this respect. An ultrasonic guidewire transmits an acoustic pulse into the body and detects the reflections of the pulse at tissue boundaries due to differences in acoustic impedance. The differing times taken for the transducer to receive the reflected pulse correspond to variations in the distance of the tissue boundaries from the ultrasonic source. By stepping, or sweeping, the ultrasonic pulses of the guidewire through a selected angle, a two dimensional ultrasound image corresponding to a map of the acoustic impedance boundaries can be obtained. The intensity and position of the reflections from these boundaries will provide information on the condition of the body tissue being imaged.

In the literature, two types of ultrasonic probes have been described for diagnostic ultrasonic imaging. The first employs a synthetic aperture technique. For example, U.S. Pat. No. 4,917,097 (Proudian et al.) and U.S. Pat. No. 5,186,177 (O'Donnell et al.) teach how an ultrasonic beam is steered electronically from a transducer using the method of synthetic aperture. Generally, this involves the sequential excitation of selected elements in an array of transducer elements. The second scans by mechanical rotation of a means to direct acoustic pulses. The mechanically rotated type includes a few subclasses. In the first subclass, either the distal (remote from the operator) transducer or a mirror is rotated from the proximal end of the catheter by an extended drive shaft with a proximal motor (U.S. Pat. No. 4,794,931 (Yock) and U.S. Pat. No. 5,000,185 (Yock)). In the second subclass, the rotation is confined to the distal end, where either a miniature motor (U.S. Pat. No. 5,240,003 (Lancee et al.) and U.S. Pat. No. 5,176,141 (Bom et al.)) or a fluid driven turbine is used to rotate the transducer or the mirror (U.S. Pat. No. 5,271,402 (Yeung and Dias)). In a third subclass, a stationary proximal transducer is acoustically coupled to a rotating acoustic waveguide that conducts the sound to the distal end (e.g., U.S. Pat. No. 5,284,148 (Dias and Melton). In another subclass, e.g., U.S. Pat. No. 5,509,418 (Lum et al.), a turbine is rotated by an acoustic signal generated outside the vascular vessel to direct another ultrasonic signal in a rotating fashion. In yet another subclass, e.g., U.S. Pat. No. 5,507,294 (Lum et al.), an external driving member rotates a tube to rotate a reflecting element at the tip of the tube to reflect ultrasound.

Currently, the most widely used type of intracavity ultrasonic probe is the mechanically rotated system with a transducer having a single planar element placed at the distal end of the catheter. A reason for this preference is the superior image quality as compared with current synthetic aperture systems. However, the mechanically rotating ultrasonic probes have some shortcomings. For an ultrasonic probe with a drive motor proximal to the operator, i.e., remote from the transducer, a drive cable encircled by a sheath is generally needed to transfer mechanical energy to the tip of the catheter containing the transducer. A long cable may not transfer energy uniformly to the catheter tip to rotate the transducer or reflector uniformly. Furthermore, the probe is liable to fail over time because of the cable's rapid and repetitive rotation within the sheath. On the other hand, when a drive motor is located near the tip of the catheter, the motor must be small. Such fragile motors are electrically and mechanically complex, making them very expensive. With mechanical parts, e.g., ball bearings, etc., that undergo rigorous motion, the motor is liable to fail. Such motorized imaging mechanisms are not desirable for used in a small imaging guidewire. What is needed is an imaging guidewire with a structurally simple actuator at the tip of the guidewire for moving a transducer or reflector to scan tissues.

SUMMARY

The present invention provides an imaging guidewire for imaging tissues from inside a patient's body cavity. The imaging guidewire is elongated and has a distal end suitable for inserting inside the body cavity, whereas the proximal end of the imaging guidewire is to remain outside the body.

The imaging guidewire includes an elongated main body portion and an end portion connected distally to the elongated main body portion. The end portion has a housing proximate to the imaging guidewire's distal end, an ultrasonic-beam-emitting assembly having a pivotable part and a driver for producing a pivotal motion on the pivotable part. The housing has at least a portion that is substantially acoustically transparent or sonolucent. The pivotable part is movable and is operatively connected to the housing, i.e., the pivotable part may be connected indirectly to the housing, for example, via an electromagnet. The pivotable part can either have mounted on it a transducer for emitting ultrasound or a reflector for reflecting ultrasound from an ultrasound source. In either case, when the pivotable part pivots it sweeps ultrasonic energy over a selected angle. The driver is located proximate to the transducer such that all driving motions for driving the pivotal motion occur proximate to the distal end of the imaging guidewire.

In the imaging guidewire of the present invention, a cable is no longer needed to transfer rotational energy from the proximal end to the distal end of the imaging guidewire as in the prior art devices. In fact, no energy needs to be transferred mechanically from the proximal end to the tip of the imaging guidewire. Since the imaging guidewire of the present invention can image tissues in a body cavity, for example, within a blood vessel, it can be advantageously inserted into a tortuous passageway with relative ease and safety. The imaging is done by scanning an acoustic beam of ultrasonic pulses over the tissues by a pivotal motion of a plate on which a transducer or a reflector is affixed. As the plate pivots, for example, the transducer mounted on the plate, wobbles back and forth, thus sweeping the acoustic beam over a selected angle. Preferably, the plate pivots on a fulcrum at about the midpoint of the plate in a back and forth rocking (or see-sawing) manner. In the preferred apparatus the fulcrum is a torsion arm that is twistable to allow the plate to pivot. Therefore, no mechanical sliding, rolling, or frictional motion on a surface exists. This reduces the risk of failure of the imaging guidewire.

Moreover, unlike motorized imaging guidewires, the electromechanical system used to drive the pivotal motion in the present invention is relatively simple. No sophisticated stator and rotor mechanism is required at the distal end of the imaging guidewire where the transducer is located. Therefore, a small driver, used for actuating the pivotal motion, can be fabricated with enhanced reliability for the imaging guidewire. This will enable the fabrication of an imaging guidewire usable in even small blood vessels or body cavities. Both forward-looking and sideward-looking transducers can be implemented in the same imaging guidewire. This facilitate faster and less traumatic insertion into the body cavity.

It is contemplated that a non-guidewire ultrasonic probe can be made with the transducer assembly of the present invention. A small ultrasonic probe can be made. The probe can be made to have forward-looking and sideward-looking transducers if desired. This obviates the need for multiple instrument exchanges if both forward-looking and sideward-looking capabilities are required, thereby reducing the time needed for the imaging process and the trauma resulting from maneuvering the catheter within the body.

BRIEF DESCRIPTION OF THE DRAWINGS

The following figures show the embodiments of the present invention to better illustrate the apparatus of the present invention. In these figures, like numerals represent like features in the several views and the drawings are not drawn to scale for the sake of clarity.

DETAILED DESCRIPTION OF THE INVENTION

The present invention provides an imaging guidewire that has an actuating mechanism proximate to the guidewire's tip, which is insertable into a patient's body. With the actuating mechanism at the tip, a long mechanical-energy-transferring system for transferring energy from a motor or a similar mechanical actuator outside the body is obviated. Thus, there is no need for cumbersome features such as cables for mechanically turning the transducer in 360° cycles in a protective shell or sheath. The guidewire is a special application of the ultrasonic probe disclosed in copending application Ser. No. 08/657,742 (filed May 31, 1996 by the same inventors as the present application), which is incorporated by reference in its entirety herein.

Figure 1:
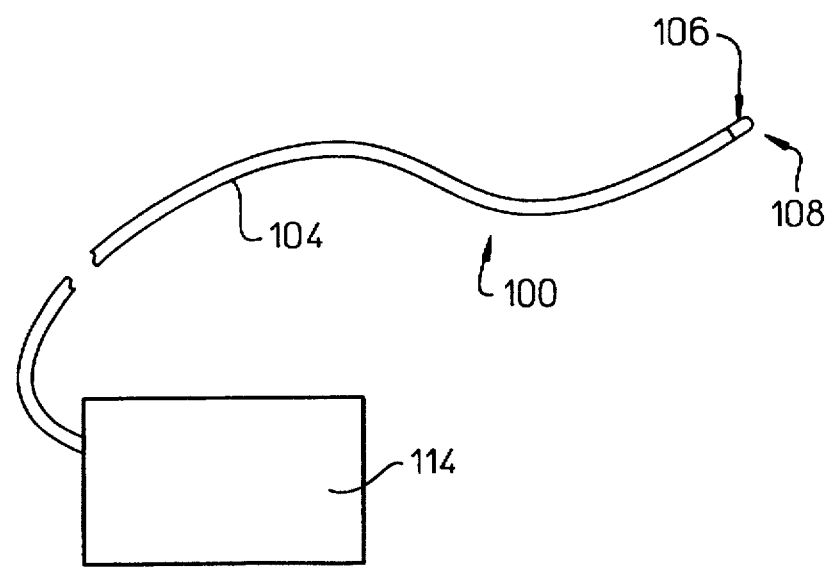
FIG. 1 shows a schematic representation of an imaging guidewire according to the present invention.

An exemplary imaging guidewire of the present invention is schematically shown in FIG. 1. The guidewire 100 has a distal end portion 102 for inserting into the patient's body cavity, e.g., an artery, and an proximal end 103 for the medical worker to control the operation of the guidewire. Between the distal end portion 102 and the proximal end 103 is an elongated main body 104. The elongated body 104 is connected to an "imaging head" 106 at the imaging guidewire's distal end 108. As used herein, the term "distal" end of the imaging guidewire refers to the end that can be inserted into a patient's body cavity, e.g., the lumen of a blood vessel. As used herein, the term "body cavity" refers to a hollow area generally surrounded by walls, although the hollow area is not necessarily entirely enclosed. Further, it is not limited to readily accessible cavities such as the oral cavity, the rectum, and the like. In the following description, a blood vessel is used as an example for the body cavity in which the imaging guidewire can be used. However, it is to be understood that the present invention can be adapted for use in a variety of body cavities, such as a chamber in the heart, esophagus, stomach, intestine, abdominal cavity, bladder, uterus, and the like.

Figure 2:
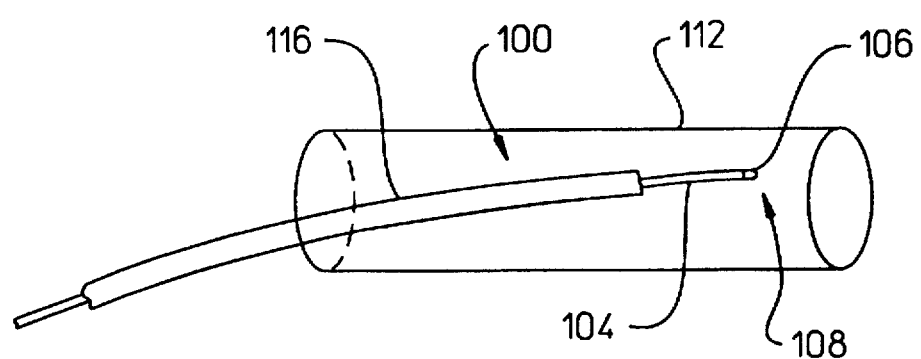
FIG. 2 shows a schematic representation of an imaging guidewire according to the present invention, showing the guidewire being deployed in a blood vessel.

FIG. 2 shows how the imaging guidewire 100 is deployed in a blood vessel 112. The imaging head 106 contains an ultrasound-emitting assembly which includes a transducer and the actuating mechanism for moving the transducer to scan an ultrasonic beam in the blood vessel 112. The ultrasonic beam is consisted of pulses. The proximal end 103, which is remote to the distal end 108, is electrically connected to an ultrasound controller 114 (see FIG. 1) that controls the emission and reception of ultrasound, as well as steering the ultrasound-emitting assembly. This controller 114 can also have the capability to analyze the electronic signals transmitted from the imaging guidewire as a result of ultrasound signals received by the imaging head 106. Preferably, the controller 114 can further store and display data. In this case, computers, CRT monitors, and the like, can be present in the controller 114.

It is preferable that the proximal end 103 is detachable from the controller so as to facilitate inserting the guidewire to a desired position in the body cavity. An elongated sheath 116 is shown surrounding a significant portion of the elongated body 104 of the imaging guidewire 100. Such a sheath, for example, can be inserted into the body cavity after the guidewire has been placed in the desired location. Such a sheath can be used for introducing various objects, e.g., angiographic catheter, pacing catheters, cutting tools for atherectomy, etc., into the body cavity. Instead of a sheath, structure 116 can also be, e.g., a catheter itself. It is contemplated that an imaging ultrasonic probe that is not a guidewire can be made, based on the present disclosure, by a person skilled in the art. Such a non-guidewire ultrasonic probe can be introduced by means of a sheath or a guidewire into the body cavity.

Figure 3A:
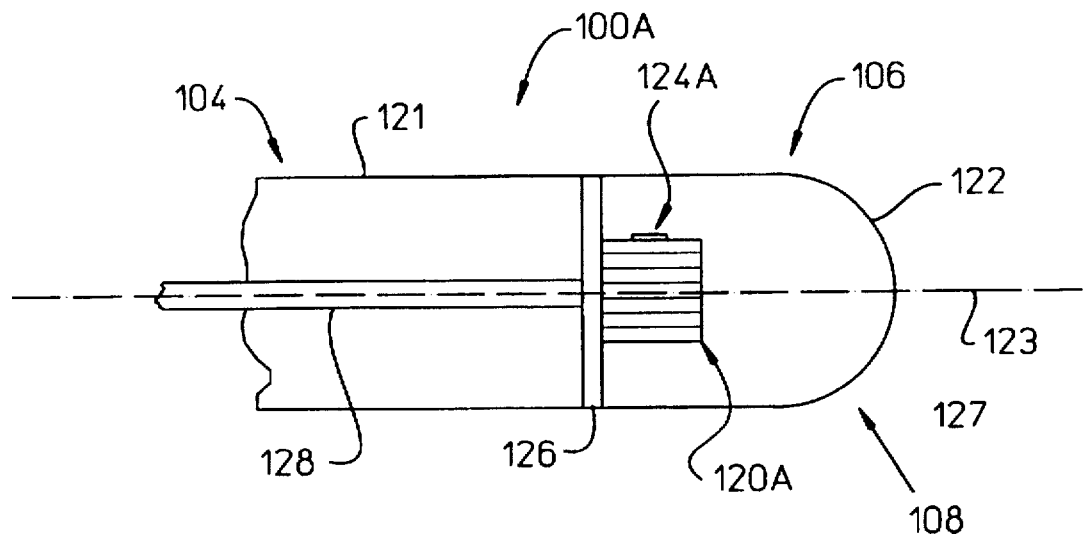
FIG. 3A shows a schematic representation of an embodiment of an imaging guidewire according to the present invention.

FIG. 3A shows further details of a portion of an embodiment of the imaging guidewire (labeled as 100A in FIG. 3A) at the distal end 108. In this embodiment, the elongated body 104 of the imaging guidewire 100A has a tubular wall 121 connected to the imaging head 106. The imaging head 106 has a housing 122, for enclosing and protecting a microactuator 120A with a pivotable transducer assembly 124A for emitting and receiving ultrasonic signals. The housing 122 is substantially acoustically transparent (or sonolucent) to ultrasound emitted by the transducer assembly 124A. Alternatively, depending on the application, the housing 122 can have a window for emitting and receiving ultrasound. A support 126 is located proximal to and supports the microactuator 120A in rigid relation to the housing 122 and the wall 121, except when the flexible nature of the wall is considered.

Figure 3B:
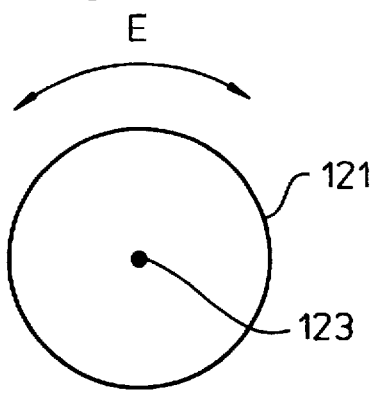
FIG. 3B is a schematic representation in axial view of the an embodiment according to FIG. 3A illustrating the direction of pivoting.

The imaging guidewire has an imaginary center line extending longitudinally along the elongated body 104. The center line of the imaging guidewire near the imaging head 106 is essentially a straight line and coincides with the longitudinal axis 123 of the distal portion of the imaging guidewire 100A. The transducer 144 (see FIG. 6) is located laterally from the microactuator 120A. As used herein, "laterally" refers to a positional relationship in a direction radial to the axis 123 of the imaging guidewire. A liquid 127 is contained in the housing 122. The liquid 127 matches the ultrasonic impedance of the housing 122 to reduce reverberations that damp the pivoting action of the microactuator 120A. The support 126 can also form a liquid-tight seal with the housing 122 to contain the liquid, although it can also be nonliquid-tight so as to allow infusion of fluid from the proximal end to the chamber defined by the housing 122. The transducer assembly 124A is generally planar and its normal points generally perpendicularly to the axis 123 of the imaging guidewire 100A. As the transducer assembly 124A emits an ultrasonic beam, the microactuator 120A rocks the transducer assembly 124A to sweep the ultrasonic beam in a plane perpendicular to the axis 123, as shown in FIG. 3B. The sweeping motion of the ultrasonic beam is shown by the two-headed arrow E.

Figure 3C:
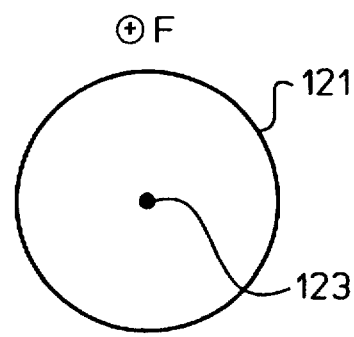
FIG. 3C is a schematic axial representation in axial view of the another embodiment according to FIG. 3A illustrating the direction of pivoting.

In an alternative embodiment, the transducer and the microactuator are arranged such that the ultrasonic beam sweeps out a plane parallel to the axis 123. The sweeping path of the ultrasonic beam is shown by the symbol ⊕, marked by F, going into the page in FIG. 3C. The wires for exciting the transducer on the transducer assembly 124A and the microactuator are located along a cable 129 inside the tubular wall 121 (see FIG. 3A). A relative stiff yet flexible wire core 128 contacts the support 126 for inserting and urging the guidewire into the body cavity. Preferably, the wire core 128 is attached to the support 126 to facilitate the insertion. Alternatively, the core 128 and the cable can be combined, e.g., the core 128 can be the core of a coaxial cable and the outside conductor of the coaxial cable can be connected to ground. The guidewire 100 has the usual structures that enable a guidewire to function well. For example, the tubular wall 121 of the guidewire includes coils to enable the guidewire to be flexible. Exemplary methods of making, methods of using, and structures of guidewires are described in, e.g., U.S. Pat. No. 5,517,989 (Frisbie et al.), U.S. Pat. No. 5,497,782 (Fugoso), U.S. Pat. No. 5,520,189 (Malinowski et al.), and U.S. Pat. No. 5,546,948 (Hamm et al.). The description on guidewires in these documents are incorporated by reference herein.

Figure 4:
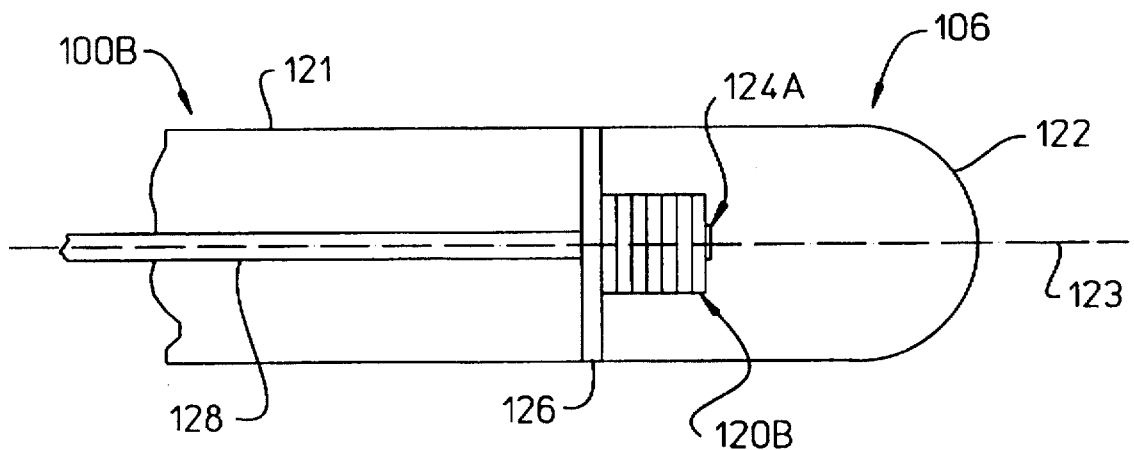
FIG. 4 shows a schematic representation of another embodiment of an imaging guidewire according to the present invention.

In another embodiment of the imaging guidewire of the present invention, the guidewire's distal portion is shown in FIG. 4, the transducer in the transducer assembly 124B is affixed distally to the microactuator 120B, thereby providing a way to scan axially, i.e., the scan angle can have a median generally along the axis 123 of the imaging guidewire.

Figure 5:
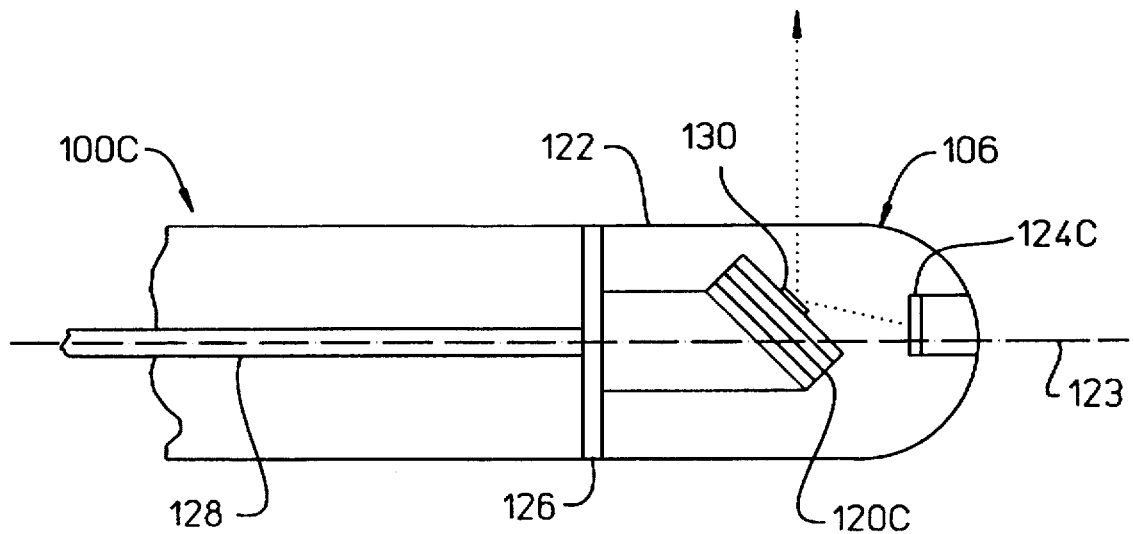
FIG. 5 shows a schematic representation of an embodiment of yet another imaging guidewire according to the present invention.

In yet another embodiment of an imaging guidewire, shown in FIG. 5, a transducer assembly 124C is supported proximate to the distal end 108 of the imaging guidewire 100C along the guidewire's axis 123. A transducer 124C emits an ultrasonic beam axially toward the proximal end. The microactuator 120C and a pivotable reflector 130 are mounted at a slanted angle to the axis 123 of the imaging guidewire such that the reflector reflects the axially-directed ultrasonic beam in a radial direction. As the reflector 130 pivots, it sweeps the ultrasonic beam to locations lateral to the imaging guidewire 100C, thereby scanning the wall of the blood vessel 112 lateral to the imaging guidewire.

Figure 6:
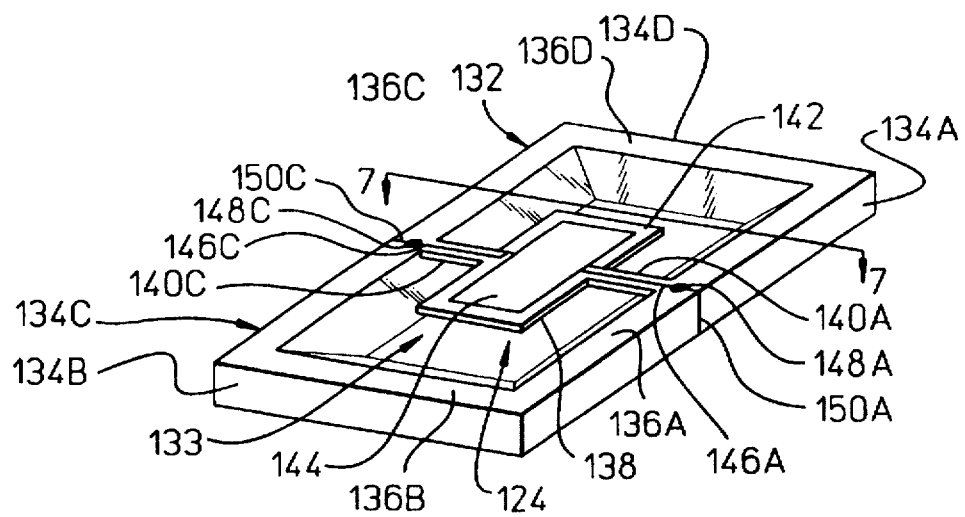
FIG. 6 shows an isometric representation of an embodiment of an imaging guidewire according to the present invention, showing the transducer in a slab-shaped stage.
Figure 7:
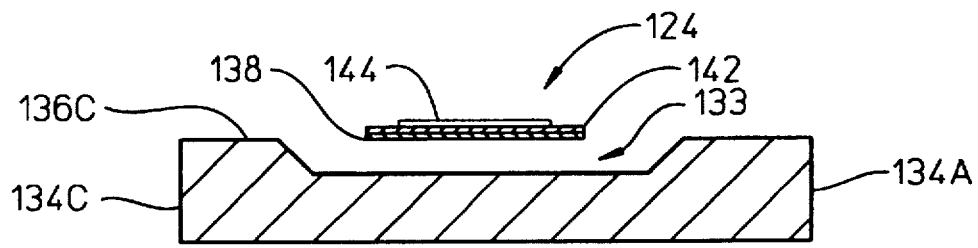
FIG. 7 shows a sectional view along line 7—7 of FIG. 6.

FIG. 6 shows a stage 132 of the imaging guidewire according to the present invention in more detail. FIG. 7 shows a sectional view of the stage 132 along the line 7—7 in FIG. 6. In this embodiment, the stage 132 is generally slab-shaped. As used herein, the term "stage" refers to the structure that includes the substrate, plate, torsion arms, magnetic material, and the transducer, which will be described below. A cavity 133 in the stage 132 is surrounded by walls 134A, 134B, 134C, 134D, on which are ledges 136A, 136B, 136C, 136D. A generally rectangular plate 138 is supported on two opposing ledges 136A, 136C by two torsion arms 140A, 140C, one located about the mid point of each opposite edge of the stage 132. A plate 138, whose thickness is much smaller than its other two dimensions, is balanced on the torsion arms 140A, 140C with the plate's center of gravity on an imaginary line joining the torsion arms. The torsion arms 140A, 140C are generally perpendicular to the thickness dimension. In this way, a minimal effort is needed to pivot, or turn, the plate on the torsion arms. If desired, the plate's center of gravity can be slightly off the torsion arms 140A, 140C without significantly affecting the performance of the imaging guidewire. As used herein, the term "transducer assembly" refers to the structure including the plate, transducer, and magnetic material, if any. The terms "pivot" and "pivotal," when referring to moving the plate or transducer assembly, describe the turning motion about supporting arms that pivot or turn as if in a pivot. Therefore, the twisting motion on torsion arms, as long as the plate or transducer assembly is observed to turn or swing as if it is on a hinge or on a pivot, is considered to be "pivotal." Because the torsion arms 140A, 140C are affixed to the walls of the stage 132, the plate 138 pivotally moves in a rocking, back and forth fashion, thereby enabling a sweeping scan by the transducer affixed on the plate.

A ferromagnetic material 142, e.g., a nickel ferrite (herein referred to as "NiFe") material, is layered on a surface of the plate 138, covering generally all of that surface. In this way, when a varying magnetic field is applied to the plate, the plate will pivot on the torsion arms instead of trying to move up and down as a whole. Due to the ease of fabrication, preferably, the magnetic material 142 is layered on the upper surface of the plate 138. As used herein, the "upper" surface refers to the surface that faces away from the cavity 133. If preferred, the magnetic material can be layered on the upper surface of the plate 138 on only one side of the torsion arms 140A, 140C, covering half of the surface.

The transducer assembly 124 includes the magnetic material 142 and a transducer 144 mounted on the upper surface of the plate 138. Electrical wires 146A, 146C extend from transducer electrodes (not shown in the figures) to connection pads 148A, 148C. The connection pads 148A, 148C in turn can be connected to electrical wires 150A, 150C to provide electrical energy to the transducer 144. Alternatively, one or more of the wires 146A, 146C, 150A, 150C can be replaced by appropriately doped channels in the torsion arms and frame of the stage, i.e., stage 132. The electrodes are connected to the surfaces of the transducer 144 to electrically generate and receive ultrasound by the piezoelectric effect. As the transducer 144 is excited and the plate 138 is pivoted by a varying magnetic field, the transducer radiates an ultrasonic beam to scan tissues in the blood vessel normal to the planar surface of the transducer.

Figure 9B:
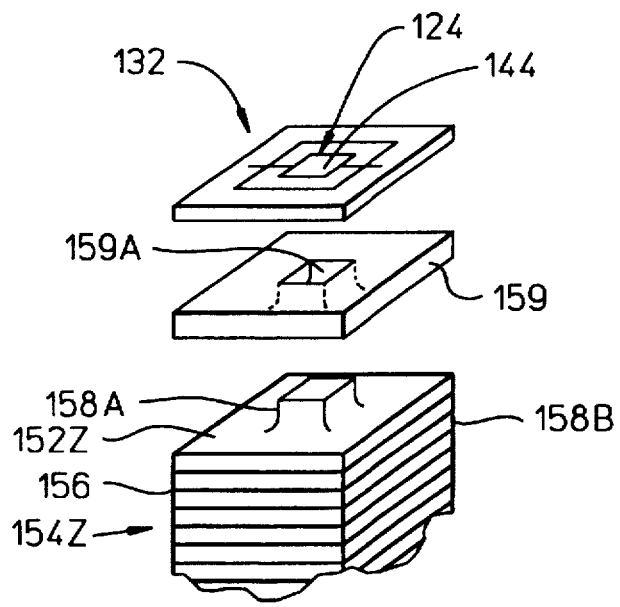
FIG. 9B shows an exploded view in portion of the microactuator of another imaging guidewire according to the present invention, showing an electromagnet with a core having a finger.
Figure 8:
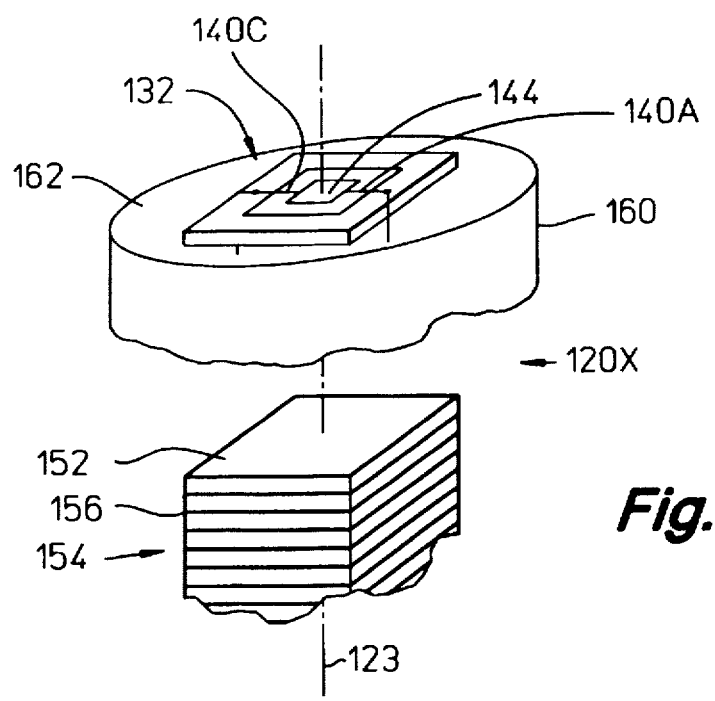
FIG. 8 shows an exploded view in portion of the microactuator of an imaging guidewire according to the present invention, showing an electromagnet.
Figure 9A:
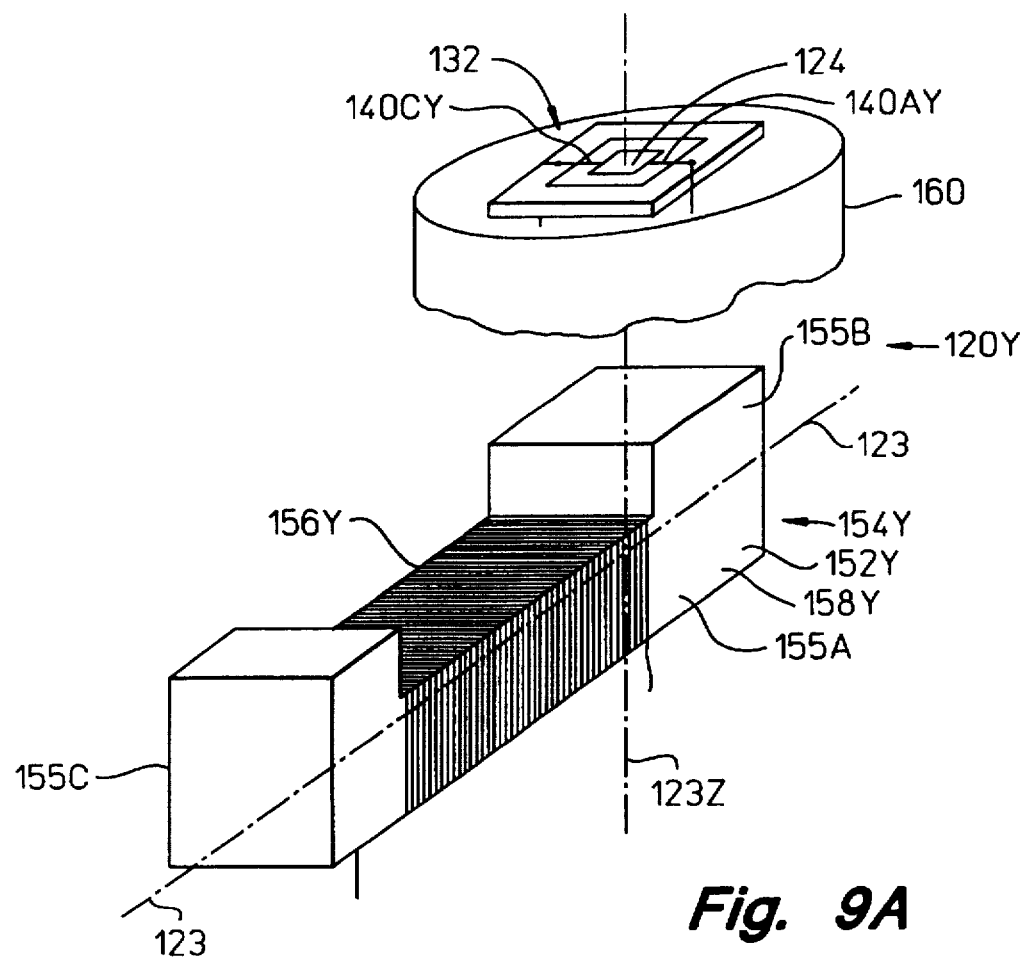
FIG. 9A shows an exploded view in portion of the microactuator of another imaging guidewire according to the present invention, showing an electromagnet.

FIG. 8 is an exploded view showing how the microactuator is located relative to the transducer. The microactuator 120X can be considered to include the stage 132 having the plate 138 (see FIG. 7) and torsion arms 140A, 140C, as well as the magnetic material 142 layered on the plate. The transducer assembly 124 is moved by the pivotal movement of the plate 138 about the torsion arms 140A, 140C caused by variations of a magnetic field in which the magnetic material is situated. An electromagnet 154 is proximate to the stage 132 to provide the varying magnetic field. The electromagnet 154 contains a coil 156 that is wrapped around a magnet core 152. An electrical current can be passed through the coil 156 to produce a varying magnetic field. The magnet core 152 of the electromagnet 154 extends parallel to, preferably along, the axis 123 of the imaging guidewire. This means that a long magnet core can be used to increased the number of turns of the coil, since the length of the electromagnet can extend along the axis 123 and is not limited by the diameter of the imaging guidewire in this embodiment. Such an actuator is suitable for use in an imaging guidewire similar to that shown in FIG. 4. The coil 156 is wrapped such that the axis of the coil is perpendicular to the plane of the stage 132 and the plate 138 is located generally at about the axis of the coil, which is parallel to the axis 123 of the imaging guidewire. In this way, the lines of the magnetic field pass through the plate 138 in a direction generally perpendicular to the plane of the stage 132. The stage 132 can be affixed to the electromagnet 154 by commonly known affixing means, such as adhesive, clips, clamps, and the like. Optionally, a tube 160 with an end plate 162 can be used to anchor and protect the stage 132 and the electromagnet 154. It is noted that if a short magnet core is used so that the electromagnet and the stage 132 can fit transversely inside the imaging head 106, this arrangement of the plate 138 with the electromagnet 154 is also applicable for an imaging guidewire of FIG. 3A FIG. 9A shows an exploded view of another embodiment of a transducer assembly and a microactuator that is especially suitable for an imaging guidewire of FIG. 3A. In this embodiment, the stage 132 is generally similar to the stage 132 of FIG. 8. The electromagnet 154Y has a U-shaped magnet core 152Y. The magnet core 152Y has an elongated magnet core body 155A with a first leg 155B and a second leg 155C extending about perpendicularly from its ends. The first leg 155B is more distal than the second leg 155C in the imaging guidewire. A coil 156Y is wrapped around the magnet core 158Y. The axis of the coil is generally parallel to the axis 123 of the imaging guidewire so that a long electromagnet can be used. The stage 132 is proximate to and preferably rests on the first leg 155B at the distal end of the imaging guidewire. In this way, the lines of the magnetic field in the electromagnet 154Y are channeled from the elongated magnet core body 155A and pass out of the first leg 155B through the stage 132. Thus, as the current passing through the coil 156Y varies, the electromagnet's magnetic field varies and pivots the plate on the torsion arms 140AY and 140CY. Again, as in FIG. 8, the electromagnet 154Y can be positioned proximate to or affixed to the stage 132. An alternative to a U-shaped magnet core is a L-shaped magnet core, which still allows the stage 132 to be placed on the leg at the distal end of the magnet core. The electromagnet with a U-shaped magnet core or a L-shaped magnet core can also be used in an imaging guidewire of FIG. 5.

The strength of the electromagnet can be increased by increasing the number of loops in the coil, increasing the cross sectional area of the magnet core (and therefore the size of the loops), and increasing the current in the coil. Since the plate 138 (see FIG. 7 and FIG. 14) is small and only magnetic field lines passing through the magnetic material on the plate affect the pivotal motion, as shown in FIG. 9B in portion, to increase the effective magnetic field strength, the electromagnet 154Z can have a magnet core 152Z including a finger 158A extending from a larger body 158B. The larger body 158B of the magnet core allows the coil 156 to have larger loops. At the finger 158A, the magnetic field lines are concentrated to pass through the magnetic material on the plate 138. Preferably, a spacer 159 having a void 159A for receiving the finger 158A can be disposed between the larger body 158B of the magnet core and the stage 132 to help secure the stage to the electromagnet 154Z. The spacer 159 can have planar dimensions generally similar to those of the stage 132.

With the above-described arrangements, the stage 132 and the electromagnet can be enclosed in the imaging head 106 without enlarging the radial dimension of the imaging head. Methods of making coils and electromagnets for microactuators are known in the art. Some methods involve using a metallic coil. e.g.. by deposition. and some involve doping a silicon material to form the conductive coil for the electromagnet. See. e.g., Wagner et al., "Microactuators with Moving Magnets for Linear, Torsional or Multiaxial Motion." *Sensors and Actuators, A*. 32, 1992. pp. 598–603; Kamins. et al.. "Diffusion of Impurities in Polysilicon." *J. Appl. Phys.*, 43 (1), January 1972. p. 83–91; Mandurah, et al.. "A Model for Conduction in Polycrystalline Silicon. Part 1: Theory," *IEEE Trans. of Electron. Devices*, Vol. ED-28. No. 10. October 1981. p. 1163–1170; whose descriptions of the methods for doping and for fabricating a microactuator are incorporated by reference herein.

In another embodiment. more than one transducer can be present in the imaging head 106. In fact, more than one stage. each positioned such that the transducer thereon directs an ultrasonic beam at a different direction, can be present. This can be done. for example, by combining the transducer assemblies of FIG. 3A and FIG. 4.

Method of Making the Apparatus

The microactuator and the transducer assembly can be made by adopting micromachining methods for semiconductors known in the art. e.g.. Judy and Muller. "Magnetic Microactuation of Torsional Polysilicon structures," *Dig. Int. Conf Solid-State Sensors and Actuators*, Stockholm, Sweden, Jun. 25–29, 1995. pp. 332–339; Ahn and Allen, "A Fully Integrated Micromagnetic Actuator with a Multilevel Meander Magnetic Core," *Tech. Dig. IEEE Solid-State Sensor and Actuator Workshop, (Hilton Head '92)*, Hilton Head Island, S.C., Jun. 22–25, 1992. pp. 14–18; Liu et al.. "Out-of-Plane Permalloy Magnetic Actuators for Delta-Wing Control," *Proc. IEEE Micro Electro Mechanical Systems (MEMS '95)*, Amsterdam. The Netherlands. Jan. 29–Feb. 2, 1995, pp. 7–12; Judy and Muller, "Magnetic Microactuation of Polysilicon Flexure Structures," *J. Microelectromechanical Systems*, 4(4), December 1995. pp. 162–169; and Pister et al. "Microfabricated Hinges," *Sensors and Actuators*, A. 33, 1992. pp. 249–256, of which the description on methods of making microactuators are incorporated by reference herein.

FIGS. 10 to 14 show how such micromachining can be done using a silicon substrate; a sacrificial layer made of, e.g., silicon dioxide ($SiO_2$) or glass; a plate and torsion arms made of. e.g., polysilicon or silicon nitride ($Si_3N_4$); and on the plate a layer of magnetic material, e.g., nickel ferrite (herein referred to as NiFe) permalloy consisting of 80% nickel and 20% iron. In scientific literature, this material with 80% nickel and 20% iron is sometimes represented by $Ni_{80}Fe_{20}$. It is noted that other magnetic materials can also be used, as long as it can be attracted by the electromagnet to pivot the plate. Briefly, a substrate with a thickness about the desired thickness of a stage 132 is provided. A layer 170 of sacrificial material, e.g., silicon dioxide, is deposited on the substrate 168, followed by a grown film 172 of either polysilicon or silicon nitride. The layer of magnetic material, e.g., NiFe, is deposited on the polysilicon or silicon nitride layer. Then, through appropriate masking and etching techniques, selected portions of the magnetic material (e.g.. NiFe 178), seed layer 174, plate material, and sacrificial layer 170 are removed to form the plate 138 and torsion arms 140A, 140C. Methods of forming such suitable layers of substrate 168, sacrificial material 170, plate material 172, and magnetic material (e.g., NiFe 178) are known in the art. Further selective etching of the silicon substrate 168 will allow the formation of a cavity 133.

An alternative to polysilicon or silicon nitride is polyimide. e.g.. PI-2611 from DuPont Company (Wilmington, Del.). A polyimide layer is typically formed by spinning. Such a layer can be etched by dry plasma etching. Polyimide materials suitable for such applications are available commercially from chemical suppliers such as DuPont Company and Ciba Geigy Corp. (Greensboro, N.C.). Methods of spinning and etching a polyimide layer are known in the art. See, e.g., Ahn, et al., "A Planar Variable Reluctance Magnetic Micromotor with Fully Integrated Stator And Wrapped Coils," *Proc. IEEE Micro Electro Mechanical Systems (MEMS '93)*, Fort Lauderdale, Fla., Feb. 7–10, 1993. A layer of such materials, e.g., silicon nitride, polysilicon, polyimide, that can be used to form the support arms is herein referred to as "transducer-support layer" since the support arms and the bottom layer of the transducer assembly are formed from such layers.

To illustrate the method of forming the stage 132 of the present invention, an embodiment that includes a silicon substrate layer, a $SiO_2$ sacrificial layer, a silicon nitride plate with torsion arms, and a magnetic material layer of NiFe is described below. It is commonly known that glass and $SiO_2$ can be etched with suitable chemicals, e.g., buffered hydrofluoric acid (HF) mixtures; silicon can be etched with potassium hydroxide (KOH) or tetramethyl ammonium hydroxide (TMAH); glass, $SiO_2$, polysilicon, and silicon nitride can be dry-etched with plasma chemistry known to one skilled in the art; and silicon nitride can also be wet-etched with phosphoric acid ($H_3PO_4$). It is also known that these etching methods affect each material (e.g., silicon, silicon nitride, polysilicon, $SiO_2$, NiFe) differently. This difference is due to the materials' inherent physical and chemical properties. The different etch rates for such materials using a wide variety of etchants will allow the ability to etch differentially one material quickly and another very slowly.

Figure 10:
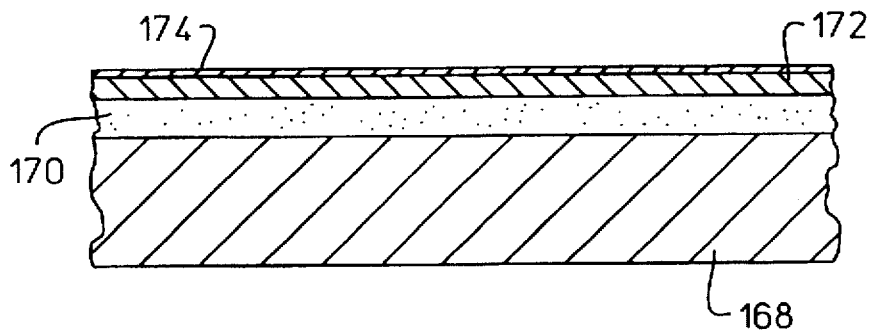
FIG. 10 shows a sectional view of layers of material during the formation of an embodiment of a stage in the fabrication of the microactuator of an imaging guidewire according to the present invention.

As an example, layers of materials shown in FIG. 10, including silicon nitride 172, $SiO_2$ 170, and silicon 168, but less the conductive seed film 174, can be considered. The Silicon nitride layer 172 can be lithographically masked and patterned with hot $H_3PO_4$ at about 50° C. The acid will etch completely through the exposed silicon nitride areas relatively quickly but the etch rate will slow down considerably, i.e., in orders of magnitude, on the exposed $SiO_2$ layer 170. The lithographic masking material on top of the silicon nitride layer can be removed by an oxygen plasma with minimal effect on the exposed $SiO_2$ layer 170. Neither will the oxygen plasma affect the exposed silicon nitride layer. At this stage of the process, the lithographic masking material on the silicon nitride has been removed and the opening in the silicon nitride layer exposes a thin layer of $SiO_2$. A brief characterized timed dip, e.g., of about 10 seconds, in a 10:1 hydrofluoric acid will remove the exposed $SiO_2$ layer 170. The final silicon substrate 168 is now exposed. A final KOH or TMAH etch can be used to etch the silicon substrate 168. The proper dilutions at the proper temperature will minimally affect the $SiO_2$ layer 170 and the silicon nitride layer 172. Proper timed exposure of the materials to TMAH or hot KOH will result in a silicon etched cavity approximately defined by the silicon nitride 172 and $SiO_2$ 170 opening.

This general process methodology will be applied to fabricate the structures of interest.

Etching methods for various materials used in solid state semiconductor technology are known in the art. For example, methods for etching silicon dioxide are described in Steinbruchel et al., "Mechanism of dry etching of silicon dioxide—A case study of direct reactive ion etching," *J. Electrochem. Soc. Solid-state and Technology*, 132(1), pp. 180–186, January 1985; and Tenney et al., "Etch Rates of Doped Oxide in Solutions of Buffered HF," *J. Electrochem. Soc. Solid State and Technology*, 120 (8), pp. 1091–1095, August 1973. Polysilicon etching is described by Bergeron et al., "Controlled Anisotropic Etching of Polysilicon," *Solid State Technologies*, August 1982, pp. 98–103; and B. L. Sopori, "A New Defect Etch for Polycrystalline Silicon," *J. Electrochem. Soc. Solid State and Technology*, 1984. Silicon nitride etching is described by van Gelder et al., "The etching of Silicon Nitride in Phosphoric Acid with Silicon Dioxide as a mask", *J. Electrochem. Soc. Solid State and Technology*, 114 (8), August 1967, pp. 869–872. Silicon etching is described by M. J. Declercq, "A New CMOS Technology Using Anisotropic Etching of Silicon," *IEEE J. of Solid State Circuits*, Vol. SC-10, No. 4, August 1975, pp. 191–196; K. E. Bean, "Anisotropic Etching of Silicon," *IEEE Trans. Electron. Devices*, Vol. ED-25, No. 10, October 1978, pp. 1185–1193; Osamu Tabata, "pH-controlled TMAH etchants for silicon micromachining," *Sensors and Actuators*, A53, 1996, pp. 335–339, and Robbins, et al., "Chemical Etching of Silicon II. The system of HF, $HNO_3$, $H_2O$, and $HC_2H_3OO_2$," *J. Of The Electrochemical Society*, 107 (2), February 1960, pp. 108–111. These etching methods are incorporated by reference herein. The transducer can also be deposited on the magnetic material layer prior to etching the silicon substrate 168.

As an illustrative example to form a plate with a transducer, as shown in FIG. 10, a $SiO_2$ sacrificial layer 170 of a desired shape, size, thickness, and pattern is formed on a silicon substrate 168. The sacrificial layer 170 is covered with a transducer-support ($Si_3N_4$) layer 172. This $Si_3N_4$ layer 172 is then covered with a photoresist, masked, and etched to form the desired size, shape, and pattern suitable to support the magnetic material and the transducer and to withstand the rigor of repeated torsional turning of the torsional arms during operation. A conductive seed film 174, e.g., containing a chromium film and a copper film, is then vapor deposited on the selected surface on the $Si_3N_4$ layer 172 to facilitate the deposition of the magnetic material.

Figure 11:
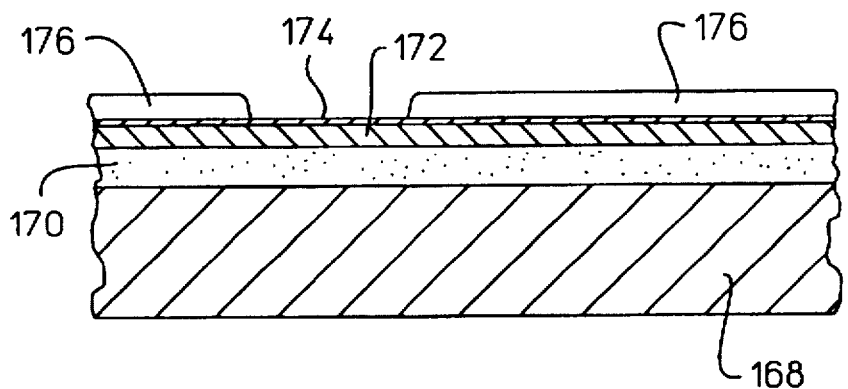
FIG. 11 shows a sectional view of layers of material during the formation of an embodiment of a stage in the fabrication of the microactuator of an imaging guidewire according to the present invention, showing the preparation of patterning a layer of magnetic material.
Figure 12:
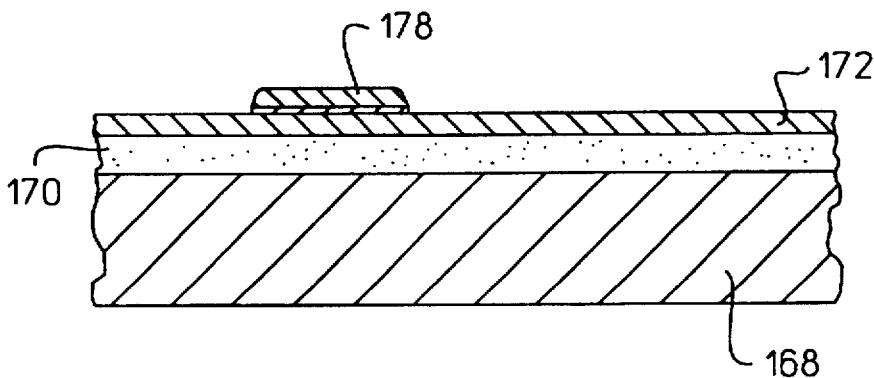
FIG. 12 shows a sectional view of layers of material during the formation of an embodiment of a stage in the fabrication of the microactuator of an imaging guidewire according to the present invention, showing a layer of magnetic material formed.

In FIG. 11, a layer of photoresist 176 is used to cover areas of the $Si_3N_4$ layer 172 on which deposition of magnetic material is not desired. A NiFe layer 178 of the desired thickness is then electroplated on the portion of the $Si_3N_4$ layer 172, i.e., on the conductive seed film 174, not covered by the photoresist 176. In FIG. 12, after removal of the photoresist and the conductive seed film 174 in selected areas, a NiFe layer of the desired size, thickness, and shape remains on the $Si_3N_4$ layer 172.

Figure 13:
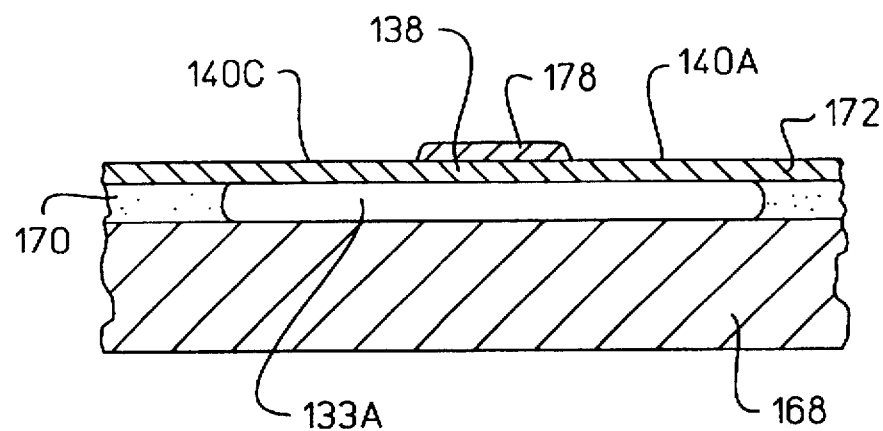
FIG. 13 shows a sectional view of layers of material during the formation of an embodiment of a stage in the fabrication of the microactuator of an imaging guidewire according to the present invention, showing the formation of a cavity in which the transducer assembly can move pivotally.
Figure 14:
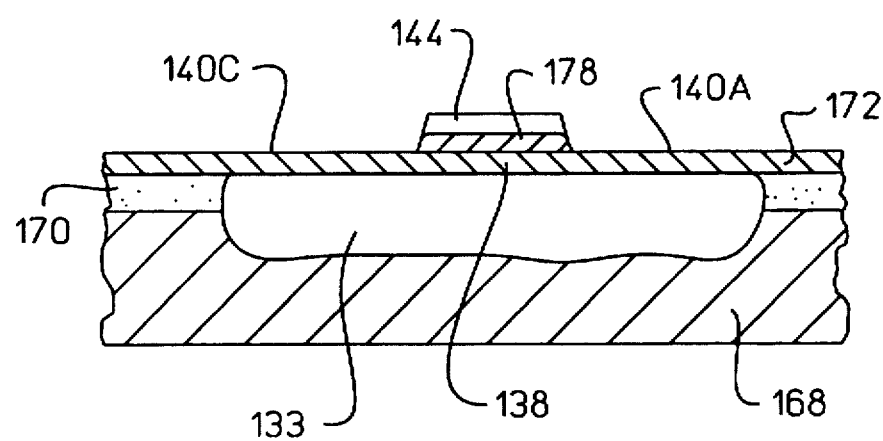
FIG. 14 shows a sectional view of layers of material during the formation of an embodiment of a stage in the fabrication of the microactuator of an imaging guidewire according to the present invention, showing a transducer disposed on the plate.

In FIG. 13, to shape the substrate 168 defining the cavity 133 (see, also FIG. 6 and FIG. 14), the sacrificial layer 170 beneath the portion of the $Si_3N_4$ layer 172 which is designated to be the plate 138 and the torsion arms is etched by HF. After etching away the selected material of the sacrificial layer 170, the desired silicon substrate area is exposed. This exposed silicon substrate area in the silicon substrate 168 can be etched with a KOH etching solution or TMAH solution to add depth to the cavity 133A. Upon completion of this etch, the cavity 133, as shown in FIG. 14, is formed. A transducer 144 can then be affixed on the plate 138. The connection pads 148A, 148C and wires 146A, 146C can be used to interface the transducer via cabling 150A, 150C to the controller 114. These steps can be done with commonly known procedures.

Depending on the application of the imaging guidewire, the size, shape, thickness, and other dimensional characteristics of the microactuator and the transducer can vary to adapt to the application. For example, an intravascular imaging guidewire will have dimensions much smaller than those of an endoscopic imaging guidewire. For intravascular imaging guidewires, the substrate 168 generally can have a thickness of about 100 to 700 μm, preferably about 400 to 500 μm. The plate 138 is preferably rectangular and have a thickness of about 2000 to 10,000 Å, preferably about 4,000 to 9,000 Å. The plate 138 can have a width of about 0.2 to 0.7 mm, preferably about 0.3 to 0.4 mm, and a length of about 0.2 to 2 mm, preferably about 0.5 to 1 mm to provide an adequate surface to support the transducer. The torsion arms 140A, 140C are preferably relatively short compared to the width of the plate so as to result in less stress due to the weight of the plate. However, the torsion arms 140A, 140C should be sufficiently long to allow the pivotal motion of the plate 138 to sweep over a desired angle, which corresponds to the angle swept by the normal of the plate. This angle is less than 180° and typically about 10° to 90°. It preferably is about ±45° with respect to the normal of the plate.

Additionally, it is preferred that the width of the plate 138 not be excessive such that the plate does not strike the base of the cavity 133. A wider plate would also require a larger force to turn the plate 138 on the torsion arms 140A, 140C and result in a slower sweep cycle. Generally, the plate 138 can vary from a square shape to a rectangular shape with a width (i.e., the side perpendicular to the torsion arms) to length ratio of about 1:3 to 1:1, preferably about 1:2. Preferably, the length is parallel to the torsional arms 140A, 140C to decrease the force needed to pivot the plate.

As previously stated, the magnetic material is preferably deposited on the upper surface of the plate 138 on both sides of the torsion arms 140A, 140C. If the layer of magnetic material, e.g. NiFe layer 178 is formed such that the N pole is on one side and the S pole is on the other side of the torsion arms 140A, 140C on the surface of the plate 138, a pole of the electromagnet (see, e.g., FIG. 8, electromagnet 154)) below the plate, when a magnetic field is applied by the electromagnet to the plate 138, it will exert an attractive force on the magnetic material on one half of the plate and an repulsive force on the magnetic material on the other half. In this way, the plate 138 is turned about the torsion arms. When the electromagnet reverses polarity, it pivots the plate 138 in the opposite way.

Preferably, to use the surface area of the plate efficiently, the magnetic material occupies substantially all of the upper surface of the plate. Its thickness is preferably less than 25% that of the plate, i.e., the $Si_3N_4$ layer. Various modifications of the above electromagnetic actuation can be contemplated. For example, the pole of the electromagnet can be placed under one side of the plate 138. Another way of actuation is to form the magnetic material on the plate 138 such that the one pole (e.g., the N pole) is on top and the opposite pole is on the bottom and place two poles of an electromagnet each under a different half of the plate.

Preferably, the transducer 144 covers substantially all of the upper surface of the magnetic material 178 and that of the plate 138 (which is not covered by the magnetic material), to use the plate's surface efficiently. The transducer 144 has the usual electrodes, wires and transducer element, as known in the art for a transducer in imaging guidewires. Methods of making small transducers for intrabody-cavity applications, such as intravascular applications, are known in the art. As an example, an intravascular imaging guidewire can have a silicon substrate layer about 500 μm thick. The $Si_3N_4$ plate can be about 9,000 Å thick, 400 μm wide, and about 1,000 μm long. The NiFe layer 178 can be about 10 μm thick and covers essentially all of the upper surface of the plate. The transducer can be made of a layer of piezoelectric material (e.g., PZT lead zirconium titanate,) of about 80 μm thick, a quarter-wave matching layer of graphite about 40 μm thick, and a thick backing material of epoxy and tungsten about 300 μm thick. It can cover essentially all of the upper surface of the plate, therefore covering the NiFe as well. The transducer may also be of quarter-wave material with an appropriate matching layer material such as graphite. Both acoustic matching and backing techniques for making transducers, as well the applicable materials, are known in the art.

The combined thickness of the transducer, the magnetic material, the sacrificial layer, and the plate is thin compared to the length and width thereof. Thus, the combined structure is still generally plate-shaped. The torsion arms 140A, 140C can each be about 5 to 20 μm long. The substrate 168 can have a thickness of about 400 to 500 μm. This will accommodate a cavity 133 of about 300 to 400 μm deep. The sacrificial layer 170 is very thin, generally about 150 to 500 Å. Therefore, the stage 132 has about the same thickness as the substrate 168.

As previously stated, the actuating mechanism and the stage 132 with the transducer assembly are located in the housing 122, which is substantially transparent to ultrasound. The housing is preferably constructed to be mechanical sturdy and has a proper thickness to withstand being manipulated in the insertion process. The guidewires of the present invention has the usual structures that allows the proper function of typical guidewires, e.g., a core to facilitate urging the guidewire into the cavity, a low-friction surface on the main body suitable for a sheath to slide on and be guided to a desire location. Commonly known techniques can be used for making such structure. Alternatively, the actuating mechanism and the stage can be made with the techniques disclosed in copending application entitled "Improved ultrasonic probe with back and forth sweeping ultrasonic source," Docket No. 10961111-1, filed by Lum et al. on the same day as the present application. The techniques of the Lum et al. copending application are incorporated by reference herein.

Operation of the Imaging Guidewire

Figure 15:
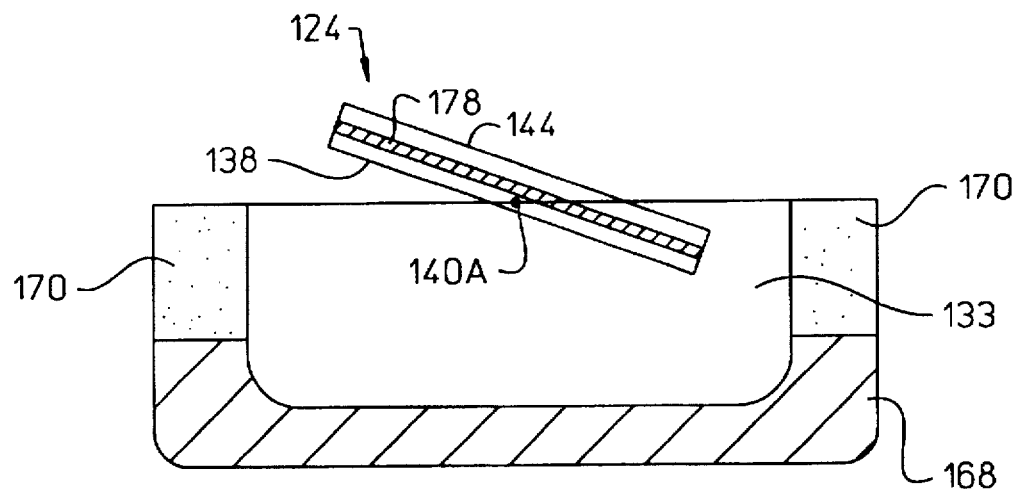
FIG. 15 shows a sectional view of an embodiment of a stage in the imaging guidewire according to the present invention, showing the plate being pivoted to face a first direction.
Figure 16:
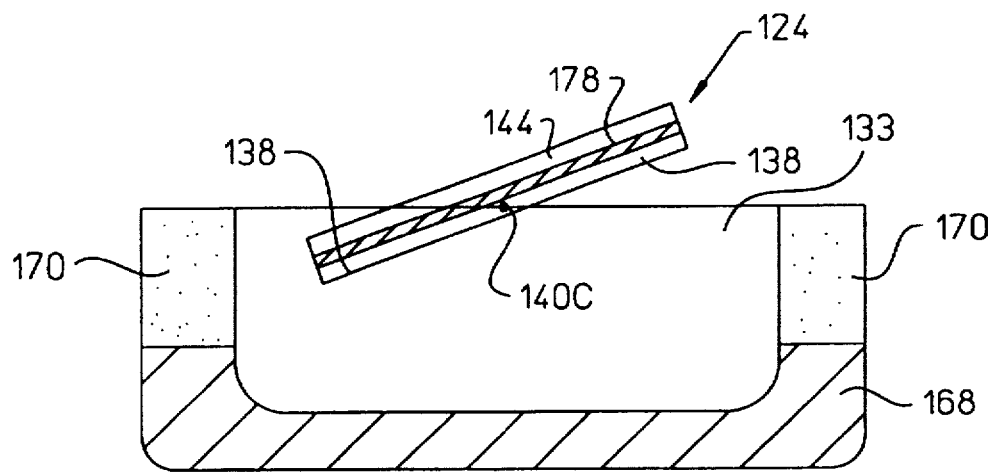
FIG. 16 shows a sectional view of an embodiment of a stage in the imaging guidewire according to the present invention, showing the plate being pivoted to face a second direction.

An imaging guidewire of the present invention can be inserted into a selected body cavity with standard methods known in the art. When an imaging guidewire of FIG. 6 or of FIG. 14 is in operation, the controller 114 (see FIG. 1) controls the current flow in the coil in the electromagnet. This causes the electromagnet (not shown in FIG. 6 or FIG. 14) to vary its magnetic field to attract or repel the magnetic material layer 178, which is ferromagnetic. FIG. 15 is a sectional view of the stage 132, with an orientation perpendicular to that of FIG. 14, showing the plate 138 being pivoted such that the plane of the plate forms an angle with the plane of the stage. This position can be achieved, for example, by passing an electrical current through the coil of the electromagnet to energize the electromagnet, thereby repelling one half and attracting the other half of the magnetic material layer 178. When the transducer element, e.g., piezoelectric element, in the transducer 144 is electrically excited, ultrasonic pulses are transmitted normal to the plane of the transducer, i.e., generally normal to the plane of the plate 138. As shown in FIG. 16, when an electric current is passed through the coil of the electromagnet in the opposite direction, the respective halves of the magnetic material layer 178 are attracted and repelled by the electromagnet to pivot the plate 138 to a different angle relative to the plane of the stage 132. As the plate 138 pivots, the transducer assembly 124 rocks on the torsion arms such that the ends of the transducer assembly swing back and forth. By repetitively cycling the pivotal motion of the plate 138, the transducer assembly 124 is swept through an angular range to scan tissues encircling the imaging guidewire.

A way to bias the plate 138 such that the transducer assembly 124 can be at a desired position when no current passes through the coil of the electromagnet is to include a permanent magnet (not shown in the figures), for example, proximate to the magnetic material layer 178. The size and strength of the permanent magnet is selected such that the constant magnetic field of the permanent magnet exerts a continuous force to bias the plate 138 to a desired position. To scan a large area, the imaging guidewire may need to be moved periodically so as to move the imaging head (labeled as 106 in FIG. 1) to different locations or orientations. This can be done, for example, by advancing or retracting the imaging head along the longitudinal axis of the guidewire and by turning the imaging guidewire on the longitudinal axis.

Figure 17:
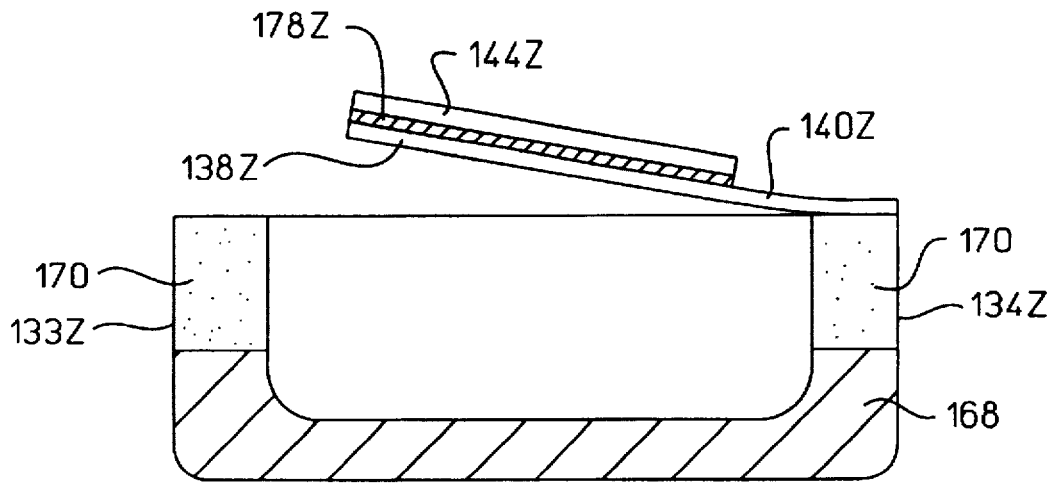
FIG. 17 shows a sectional view of another embodiment of a stage in the imaging guidewire according to the present invention, showing a flap that is supported at the flap's end.

An alternative embodiment of the imaging guidewire of the present invention, shown in FIG. 17, includes a flap 138Z linked and supported at one end by support arm(s) 140Z to a wall 134Z surrounding a cavity 133Z. This flap 138Z functions similarly to the plate 138 of FIG. 16 and supports a magnetic material layer 178Z and a transducer 144Z. Such a device can be made, for example, with the method described in Liu, et al. (1995), supra or the method described by Judy and Muller (1995), supra for making microactuators with supporting beams or cantilevers. Again, a permanent magnet can be used to bias the transducer assembly to a desired location when the electromagnet is not activated.

A transducer, e.g., transducer 144, can be used to both transmit and receive ultrasonic signals. As previously stated, the controller 114 is used to control the emission of ultrasonic signals and analyze ultrasonic signals received. Systems for controlling, emission, reception, and analysis of ultrasonic signals are known in the art.

Figure 18:
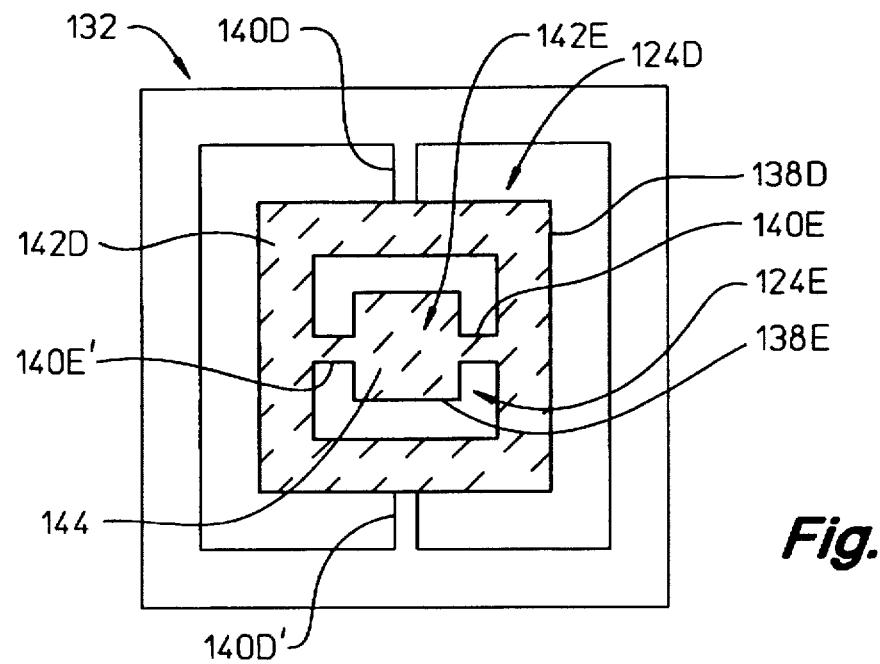
FIG. 18 is a schematic representation of a plan view of a stage according to the present invention, showing a gimbaled transducer assembly.
Figure 20:
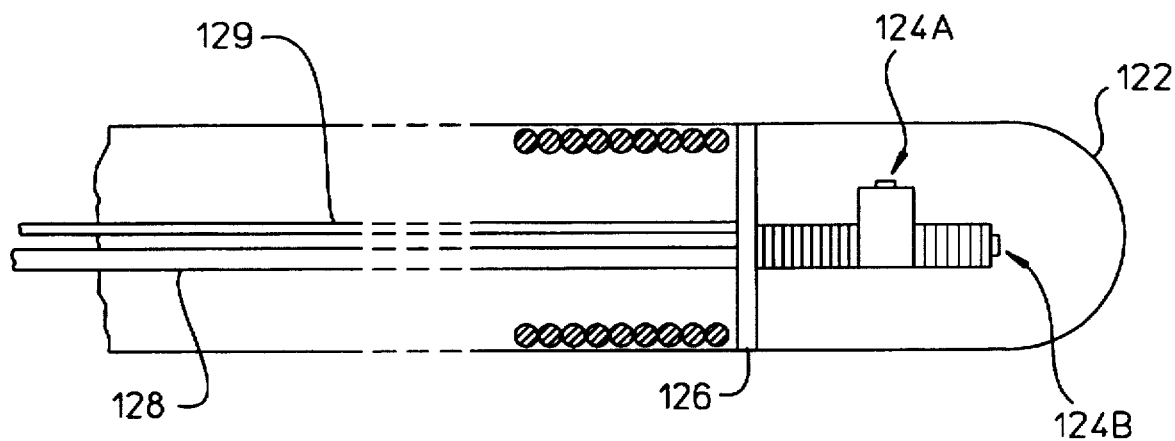
FIG. 20 shows a schematic representation of an embodiment of the guidewire of the present invention having two transducers and flexible coil near the distal tip.

FIG. 18 illustrates an embodiment in which the stage 132 has a gimbaled transducer assembly 124D in which the a first plate 138D and a second plate 138E each pivots about an axis 90° to each other. The plate 138D rocks on torsion arms 140D and 140D', causing the transducer assembly 124D to rock as a whole. At the center of transducer assembly 124D, a transducer subassembly 124E, which includes the second plate 138E, pivots on torsion arms 140E, 140E'. The transducer subassembly 124E also has a transducer 144 covering the upper surface thereof. The torsion arms 140D, 140D' are aligned with each other but are perpendicular to the torsion arms 140E, 140E', which are aligned with each other. In the transducer subassembly 124E, a layer 142E of magnetic material can be deposited on the second plate 138E, a different pole on each side of the torsion arms 140E, 140E'. Similarly, in the transducer assembly 124D, a layer of magnetic material 142D can be deposited on the first plate 138D outside the transducer subassembly 124E. By applying magnetic fields to the transducer assembly 124D and the transducer subassembly 124E separately by means of electromagnets, the transducer can be pivoted to rock on torsion arms 140D, 140D' and on torsion arms 140E, 140E'. One way to apply magnetic fields separately is by means of an electromagnet that has two concentric coils such that the inner coil controls the magnetic field for the transducer subassembly 124E and the outer coil controls the magnetic field of the transducer assembly 124D while canceling out in whole or in part the magnetic field over the transducer subassembly. An alternative way to actuate the pivotal motion of the transducer on the torsion arms 140D, 140D' and on torsion arms 140E, 140E' is by electrostatically attracting different portions of the plates 138D and 138E by adapting the electrostatic mechanism depicted in FIG. 19, which is described below. This can be done, for example, by positioning a mesa under each half of the plates 138D and 138E and orchestrating the charging of each mesa to attract various portions of the plates. Thus, an imaging guidewire can be made such that it can scan, i.e., to image, three-dimensionally without its head 106 (see FIGS. 1 and 2) being moved. However, it is contemplated that when a large area in the body cavity is to be imaged, the imaging guidewire would have to be moved to different locations in the body cavity.

Figure 19:
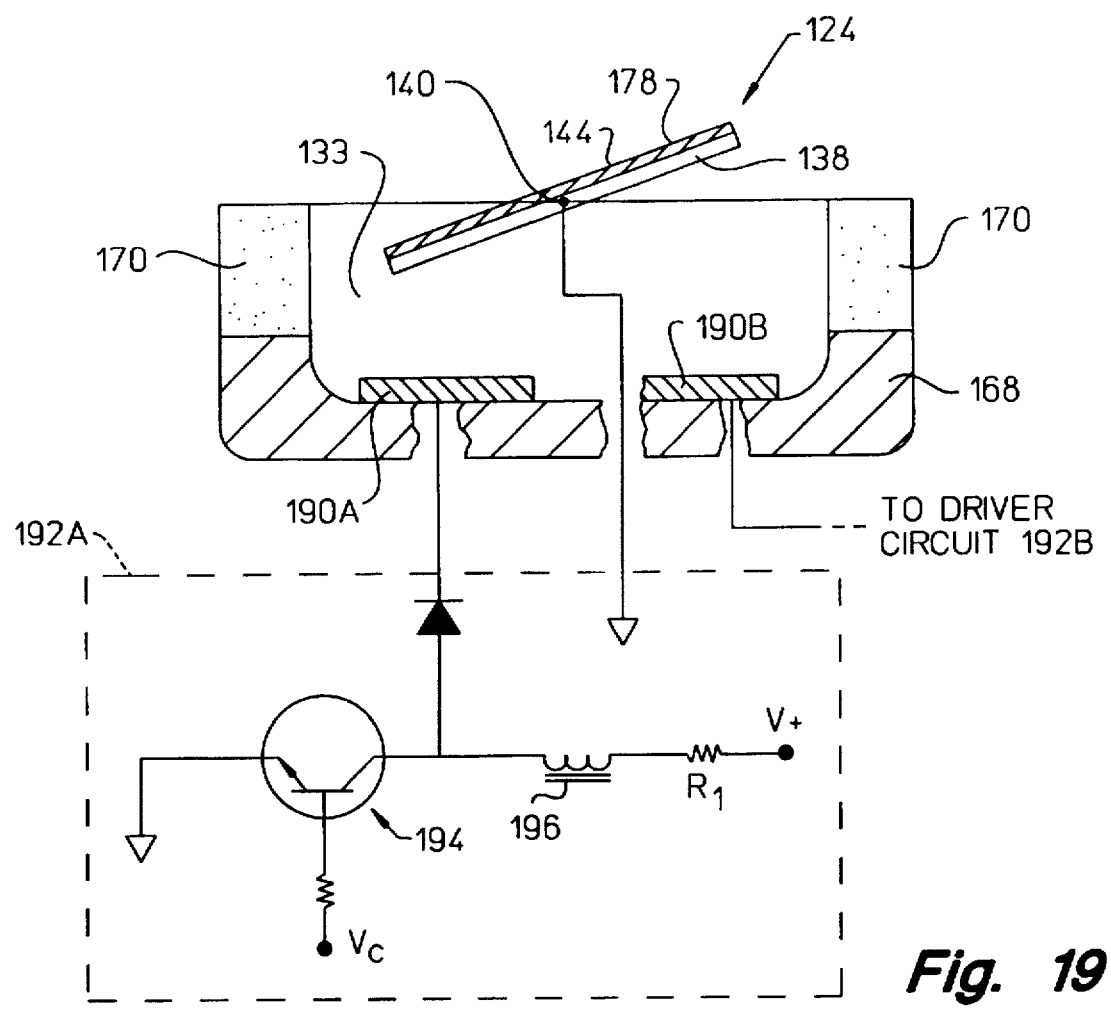
FIG. 19 is a schematic representation of a stage and an electrostatic actuation system according to the present invention.

An alternative to actuation by magnetic force is by electrostatic force. As used herein, the term "electrostatic force" refers to an attracting or repelling force resulting from the electric field of two charged bodies in proximity but not in contact. FIG. 19 illustrates an example. In this embodiment, the construction of the substrate 168, the sacrificial layer 170, the plate 138, and the transducer assembly 124 are similar to that of FIG. 16 except that no magnetic material is deposited on the plate. A metallic conductive mesa 190A, e.g., made with Pd/Ag alloy, is affixed on the substrate 168 underneath the plate 138 on one side of the torsion arm 140. A second metallic conductive mesa 190B is on the substrate on the other side of the torsion arm 140. An electrostatic driver 192A applies an electrostatic force, acting on the mesa 190A to pivot the plate 138.

An example of the electrostatic driver 192A is shown in FIG. 19. However, one skilled in the art will know that other circuitries can be constructed to perform the actuating function. A control voltage $V_c$ drives the transistor 194 by means of a control pulse. When the control voltage is high, the transistor is saturated and the current in the inductor 196 reaches a steady-state value, which depends on the supply voltage, $V_+$ and the resistor $R_1$. When the control voltage is low, the transistor 194 is turned off and the inductor causes charge to be transferred through the diode and onto the mesa 190. The plate 138 and mesa 190A act as plates of a capacitor and the electrostatic force between them causes them to be attracted to each other. The plate 138 returns to its neutral position as charge bleeds off through leakage paths, whereupon the second mesa 190B on the opposite side attracts the plate in the opposite direction. The second mesa 190B is controlled by a driver circuit 192B similar to electrostatic driver 192A such that the drivers coordinate to alternately attract their corresponding halves of the plate 138. Thus, by controlling the applied control voltage, e.g., $V_c$, the plate 138 can be pivoted back and forth. Methods of microfabricating small electrostatic microactuators are known in the art. See, for example, Garabedian et al., "Microfabricated surface plasmon sensing system," *Sensors and Actuators*, A, 43 (1994), pp. 202–207 and Richards et al., "Surface-plasmon excitation using a polarization-preserving optical fiber and an index-matching fluid optical cell," *Applied Optics*, 32(16) (1993), pp. 2901–2906.

Although the illustrative embodiments of the device of the present invention and the method of using the device have been described in detail, it is to be understood that the above-described embodiments can be modified by one skilled in the art, especially in sizes and shapes and combination of various described features without departing from the scope of the invention.

What is claimed is:

1. Imaging guidewire for imaging tissues from inside a patient's body cavity having a wall, the imaging guidewire having a distal end suitable for inserting inside the body cavity and a proximal end opposite the distal end, comprising:

(a) elongated main body portion; and
   (b) end portion connected distally to the elongated main body portion, comprising:
   (i) housing having a portion that is substantially transparent to ultrasound, the housing being proximate to the distal end of the imaging guidewire;
   (ii) an ultrasonic beam transmitting means in the housing for transmitting an ultrasonic beam, the means having a transducer for emitting the ultrasonic beam and a pivotable member which directs the ultrasonic beam to a selected direction, the pivotable member being supported by support arms operatively connected in the housing, said support arms by torsion or flexion allowing the pivotable member's back and forth pivotal motion for scanning the ultrasonic beam at the wall of the body cavity for imaging; and
   (iii) driver in said housing for driving the pivotal motion of the pivotable member, the driver being located proximate to the transducer such that all driving motions occur proximate to the distal end of the imaging guidewire.

2. The imaging guidewire according to claim 1 wherein the elongated main body portion has a surface on which a sheath can slide to be guided along the guidewide to a desired location.

3. The imaging guidewire according to claim 1 wherein the pivotable member is plate-shaped and having torsion arms which are connected to a stationary support affixed in the housing, said supporting arms being flexible or twistable to allow the pivotal motion of said pivotable member.

4. The imaging guidewire according to claim 3 wherein the pivotable member has a supporting arm made mostly of a material selected from the group consisting of polysilicon, silicon nitride, and polyimide.

5. The imaging guidewire according to claim 3 wherein the pivotable member has a reflector for reflecting the ultrasonic beam or has said transducer for emitting the ultrasonic beam to direct said beam to the selected direction.

6. The imaging guidewire according to claim 1 wherein the driver has one of an electrostatic means and an electromagnet for driving the pivotal motion to scan the ultrasonic beam.

7. The imaging guidewire according to claim 1 wherein the driver has no rotational mechanism for driving a rotational motion in the ultrasonic beam transmitting means to scan the ultrasonic beam in 360° cycles.

8. The imaging guidewire according to claim 1 wherein the ultrasonic beam transmitting means comprises two transducers each having a normal and wherein the normals of the transducers are directed to different directions.

9. The imaging guidewire according to claim 1 wherein the ultrasonic beam transmitting means includes an ultrasonic reflector pivotally movable on a fulcrum and operatively connected to in the housing to reflect an ultrasonic beam for scanning the ultrasonic beam.

10. The imaging guidewire according to claim 1 wherein the pivotable member includes a transducer and has a median such that the pivotable member pivots at about the median to scan an ultrasonic beam, and the driver includes a layer of magnetic material on the pivotable member such that the pivotable member pivots in response to a varying magnetic field.

11. The imaging guidewire according to claim 1 wherein the pivotable member is operatively connected in the housing to pivot on at least two fulcrums to scan three-dimensionally.

12. The imaging guidewire according to claim 1 wherein the transducer has a median and is part of the pivotable member to pivot at about the median to scan an ultrasonic beam, and the driver is adapted to pivot the pivotable member by a varying electrostatic force.

13. The imaging guidewire according to claim 1 wherein the support arm is supported by a support stationary relative to the housing, and wherein the pivotable member, the support arm, and the support are integrally connected.

14. Imaging guidewire for imaging tissues from inside a patient's body cavity having a wall, the imaging guidewire being elongated and having a distal end suitable for inserting inside the body cavity and a proximal end opposite the distal end, comprising:

(a) elongated main body portion; and
   (b) end portion connected distally to the elongated main body portion, comprising:
      (i) housing having a portion that is substantially transparent to ultrasound, the housing being proximate to the distal end of the imaging guidewire and being connected by coil to the elongated main body portion to enable the end portion to be flexible;
      (ii) plate-shaped member with a transducer and having a medium, operatively connected and pivotally supported by torsion arms in the housing, pivotable in a back and forth pivotal motion at about the medium to transmit an ultrasonic beam for scanning the body cavity for imaging; and
      (iii) electromagnetic driver for driving the pivotal motion of the plate-shaped member with a varying magnetic field, the driver being located proximate to the transducer such that all driving motions for driving the pivotal motion occur in the housing proximate to the distal end of the imaging guidewire, the driver further having a magnetic material connected to the transducer on both sides of the median such that the magnetic material responds to the varying magnetic field of the driver to move the transducer in a rocking manner; said imaging guidewire's distal end being of a size insertable into the patient's blood vessel.

15. A method for imaging tissues from inside a patient's body cavity having a wall, comprising:

(a) inserting into the body cavity a guidewire having a transducer positioned in a housing at the guidewire's inserting end;
   (b) generating an ultrasonic beam with the transducer; and
   (c) moving a plate-shaped ultrasound transmitter back and forth pivotally on support arm by flexion or torsion to swingingly scan the ultrasonic beam in the body cavity for imaging.

16. The method according to claim 15 further comprising urging the guidewire into the body cavity by pushing a core to direct the movement of a floppy tip having a coil in the guidewire.

17. The method according to claim 15 further comprising moving the plate-shaped ultrasound transmitter to move a reflector, which is a part of the plate-shaped ultrasound transmitter, in a back and forth manner to reflect an ultrasonic beam to scan the ultrasonic beam in a sweeping manner.

18. The method according to claim 15 further comprising mechanically driving the swinging scanning motion of the ultrasonic beam with a driver located proximate to the transducer such that all mechanical driving motions for driving the swinging scanning motion occur proximate to the inserting end of the imaging guidewire.

19. The method according to claim 15 further comprising electromagnetically driving the scanning of the ultrasonic beam.

20. A method of making an imaging guidewire for imaging tissues from inside a patient's body cavity having a wall, the imaging guidewire having an end suitable for inserting into the body cavity, comprising:

(a) providing an end portion housing;
   (b) operatively pivotally connecting an ultrasonic beam transmitter having a pivotable member by means of support arm to a support in the housing of the imaging guidewire at the inserting end thereof such that the pivotable member can swing back and forth on the support arm by torsion or flexion of the support arm for scanning an ultrasonic beam emitted from a transducer in the transmitter; and
   (c) connecting said end portion housing and said transmitter to an elongated body to link them mechanically and to provide electrical communication between said transmitter and said elongated body, the elongated body having a surface suitable to guide a sheath thereon.

21. The method according to claim 20 further comprising positioning a driver for driving the pivotal motion of the pivotable member in the housing, the driver being located proximate to the transducer such that all driving motions that drive the pivotal motion occur proximate to the inserting end of the imaging guidewire.

22. The method according to claim 20 further comprising forming the support arm by masking and etching techniques.

23. The imaging guidewire according to claim 1 wherein the end portion is connected with a coil to the elongated main body portion to enable the end portion to be flexible and wherein the guidewire further comprises a core extending through the elongated main body portion and the end portion for urging the guidewire to movement in a cavity.

* * * * *